United States Patent
Nisson et al.

(10) Patent No.: US 6,776,174 B2
(45) Date of Patent: Aug. 17, 2004

(54) APPARATUS FOR WASHING MAGNETIC PARTICLES

(76) Inventors: Paul E. Nisson, 9504 Appeals Pl., Gaithersburg, MD (US) 20886; Michael W. Schuette, 912 Park St., SE., Vienna, VA (US) 22180; Wu Bo Li, 11909 Riding Loop Ter., N. Potomac, MD (US) 20878

( * ) Notice: Subject to any disclaimer, the term of this patent is extended or adjusted under 35 U.S.C. 154(b) by 0 days.

(21) Appl. No.: 10/141,971

(22) Filed: May 10, 2002

(65) Prior Publication Data

US 2002/0174878 A1 Nov. 28, 2002

Related U.S. Application Data

(62) Division of application No. 09/377,700, filed on Aug. 20, 1999, now abandoned.
(60) Provisional application No. 60/097,487, filed on Aug. 21, 1998.

(51) Int. Cl.$^7$ .................................................. B08B 3/04
(52) U.S. Cl. .................... 134/104.4; 134/201; 366/273; 366/274
(58) Field of Search .................... 134/1, 201, 104.4, 134/25.1, 32, 42; 366/220, 273, 274; 210/222

(56) References Cited

U.S. PATENT DOCUMENTS

| | | |
|---|---|---|
| 3,750,243 A | 8/1973 | Prentice |
| 3,787,034 A | 1/1974 | Shvartsman et al. |
| 3,848,363 A | 11/1974 | Lovness et al. |
| 3,869,251 A | 3/1975 | Tsantker et al. |
| 3,892,908 A | 7/1975 | Lovness |
| 3,995,835 A | 12/1976 | Cichy et al. |
| 4,188,907 A * | 2/1980 | Lipani |
| 4,191,591 A | 3/1980 | Bender et al. |
| 4,310,253 A | 1/1982 | Sada et al. |
| 4,366,358 A * | 12/1982 | Inoue |
| 4,465,377 A | 8/1984 | de Bruyne |
| 4,472,275 A | 9/1984 | Yano |
| 4,522,501 A * | 6/1985 | Shannon |
| D280,130 S * | 8/1985 | Harkins et al. |
| 4,602,997 A * | 7/1986 | Sandulyak et al. |
| 4,720,025 A | 1/1988 | Tatevosian et al. |

(List continued on next page.)

FOREIGN PATENT DOCUMENTS

WO    WO 90/14891    12/1990

OTHER PUBLICATIONS

*DYNAL MPC®–9600: Magnetic Particle Concentrator For Microtubes in Standard Microplate Format*, 3 pages, Copyright 1994, Dynal A.S., Oslo, Norway.
*Instruction Manual: GeneTrapper™ cDNA Positive Selection System*, Cat. No. 10356–020, 30 pages, Life Technologies, published Jun. 1998.

Primary Examiner—Frankie L. Stinson
(74) Attorney, Agent, or Firm—Sterne, Kessler, Goldstein & Fox P.L.L.C.

(57) ABSTRACT

An apparatus for washing magnetic particles including a well plate for receiving an array tube holder having x rows of tubes, each tube containing magnetic particles, the well plate having (x+1) rows of wells for enabling the array tube holder to be shifted from a first position to a second position. The apparatus also includes ((x/2)+1) rows of magnets asymmetrically positioned within the well plate adjacent to the rows of wells. Placing the array tube holder in the first position causes magnetic fields produced by each magnet to attract the magnetic particles in the x rows of tubes to one side of each tube, and shifting the array tube holder to the second position reverses the magnetic fields, causing the magnetic particles to stream across to the other side of each tube. The array tube holder may be a 96 tube array tube holder (8 rows by 12 columns) in which case, the well plate includes 108 wells (9 rows by 12 columns) for simultaneously washing 96 tubes.

10 Claims, 6 Drawing Sheets

U.S. PATENT DOCUMENTS

| | | | |
|---|---|---|---|
| 4,793,973 A | | 12/1988 | Ringrose |
| 4,895,650 A | * | 1/1990 | Wang |
| 4,910,148 A | | 3/1990 | Sorensen et al. ........ 435/317.1 |
| 4,936,687 A | * | 6/1990 | Lilja et al. |
| 4,988,618 A | * | 1/1991 | Li et al. |
| 5,120,135 A | | 6/1992 | Ullman |
| 5,147,529 A | * | 9/1992 | Lee et al. |
| 5,222,808 A | * | 6/1993 | Sugarman et al. |
| 5,264,042 A | | 11/1993 | Wells et al. |
| 5,318,914 A | * | 6/1994 | Matte et al. |
| 5,458,785 A | * | 10/1995 | Howe et al. |
| 5,512,439 A | | 4/1996 | Hornes et al. ................. 435/6 |
| 5,558,839 A | * | 9/1996 | Matte et al. |
| 5,567,326 A | * | 10/1996 | Ekenberg et al. |
| 5,571,481 A | * | 11/1996 | Powell et al. |
| 5,580,524 A | * | 12/1996 | Forrest et al. |
| 5,699,842 A | | 12/1997 | Wegman |
| 5,705,062 A | * | 1/1998 | Knobel |
| 5,770,461 A | | 6/1998 | Sakazume et al. |
| 5,779,907 A | * | 7/1998 | Yu |
| 5,816,058 A | | 10/1998 | Lee et al. |
| 5,897,783 A | * | 4/1999 | Howe et al. |
| 5,976,369 A | * | 11/1999 | Howe et al. |
| 5,985,671 A | * | 11/1999 | Leistner et al. |
| 6,015,532 A | | 1/2000 | Clements et al. |
| 6,033,574 A | * | 3/2000 | Siddiqi |
| 6,193,892 B1 | | 2/2001 | Krueger et al. |

\* cited by examiner

APPARATUS FOR WASHING MAGNETIC PARTICLES

The application is a divisional of Application Ser. No. 09/377,700, filed Aug. 20, 1999, now abandoned, which claims priority to U.S. Provisional Patent Application No. 60/097,487, filed Aug. 21, 1998.

BACKGROUND AND SUMMARY OF THE INVENTION

The present invention relates generally to life sciences applications, and more particularly to an apparatus for efficient washing of magnetic particles in molecular biology/immunology applications. One such application is cDNA molecule isolation.

One approach for cDNA clone isolation requires the use of streptavidin-coated magnetic particles (approximately 1 $\mu$m in size) to capture biotinylated-oligo cDNA hybrids, which are subsequently made double stranded and transformed into a cell such as E. coli. A time consuming portion of this approach is the cDNA Capture procedure. During the cDNA Capture procedure, extensive washing of the streptavidin-coated magnetic particles are performed after the capture of the cDNA molecules. See generally The GeneTrapper™ cDNA Positive Selection System Instruction Manual, Life Technologies Inc., which is incorporated herein by reference in its entirety.

Conventionally, the cDNA Capture procedure uses six 1.7 ml tubes and a six-position magnet to attract the magnetic particles to one side of each of the 1.7 ml tubes. During the cDNA Capture procedure, the nucleic acid containing mixture (comprising a cDNA library hybridized to biotinylated-oligonucleotides) is mixed with the streptavidin-coated paramagnetic beads by gently pipetting. The suspension is incubated for 30 minutes at room temperature. During this process, the suspension is gently mixed every two to three minutes by finger tapping or vortexing at the lowest speed for ten seconds to re-suspend the beads. The tubes are then inserted into the magnet for two minutes and the supernatant is removed and discarded. Finally, the beads are extensively washed.

The extensive washing procedure consists of adding 100 $\mu$l of wash buffer to the beads, re-suspending the beads by finger tapping or gently vortexing at the lowest speed, and re-inserting the tubes into the magnet for two minutes. The supernatant is removed and discarded, and this process is repeated.

An additional 100 $\mu$l of wash buffer is added to the beads. The beads are resuspended by pipetting. The solution is then transferred to clean tubes and the clean tubes are inserted into the magnet for five minutes. The supernatant is removed and discarded and 100 $\mu$l of wash buffer is immediately added to each tube. Each tube is then finger tapped or vortexed and the tubes are again inserted into the magnet for five minutes. After the five minute incubation, the supernatant is removed and discarded, and 20 $\mu$l of 1x elution buffer is added to the beads and mixed by pipetting. The beads are incubated for five minutes at room temperature. During the incubation, the beads are finger tapped for ten seconds every minute. The tubes are then inserted into the magnet for an additional five minutes. The supernatant (which now contains the captured cDNA molecules) is transferred and saved in fresh tubes.

Throughout the above defined processes, the tubes are inserted into the magnet and, after a 2–5 minute wait period, the supernatant is removed from the tube and a solution (TE buffer, wash buffer, or elution buffer) is added to the tube by pipetting. Each 1.7 ml tube is then handled separately in order to re-suspend the paramagnetic beads after they have been pulled to one side of the tube by the magnet. This process requires picking up each tube individually and agitating the tube by finger tapping or gently vortexing the tube at the lowest speed to avoid splashing beads to the sides of the tube. The tube is then re-inserted into the magnet for an additional 2–5 minutes and the supernatant is then removed.

This process, which is repeated a number of times throughout the procedure for cDNA molecule isolation, is time consuming and can take up to approximately 45 minutes for each tube. Also, the process of finger tapping permits inconsistencies and variability between tubes.

An efficient means for simultaneously washing magnetic particles in a plurality of tubes, without finger tapping or vortexing, that renders consistent test results is needed.

The present invention satisfies the above mentioned needs by providing an apparatus that can efficiently wash multiple tubes, preferably 96 tubes, simultaneously within 5 minutes without having to individually finger tap or vortex the tubes. As will be evident, the present invention also provides high throughput operation as well as automation for any application which utilizes magnetic particles, particularly magnetic or paramagnetic beads.

The present invention is an apparatus for washing magnetic or paramagnetic particles, such as might be useful in life sciences applications, including molecular biology/immunology applications. The present invention includes a well plate which preferably has a substantially flat upper surface, a substantially flat lower surface, and a plurality of wells uniformly placed in rows and columns. Each of the wells has an opening in the upper surface of the well plate that preferably tapers conically to a lower end. The upper surface of the well plate preferably has a recessed area extending around the perimeter and through the first and last rows of the plurality of wells for receiving an array tube holder, preferably a 96 array tube holder. According to a preferred embodiment, the array tube holder can be placed in one of two positions, i.e. a first position and a second position. The array tube holder holds tubes, preferably 0.2 ml tubes, containing a solution comprising magnetic or paramagnetic particles. The lower surface of the well plate preferably includes an asymmetrical arrangement of a plurality of slots positioned in rows and columns. The first row of slots is preferably placed between an edge of the well plate and the first row of wells. Subsequent rows of slots are placed between the remaining rows of wells.

The present invention further comprises a plurality of magnets inserted into each slot in the lower surface of the well plate. Each magnet is positioned adjacent to the lower end of a well for attracting the magnetic particles in the tube toward one side of the tube. In each adjacent row of tubes, the magnetic particles are attracted to the opposite side of the tubes. A base plate is preferably attached to the lower surface of the well plate for securing the magnets.

The present invention may be used to wash or move the magnetic particles by attracting the magnetic particles to one side of the tube by placing the array tube holder in either the first position or the second position and pipetting a washing solution into each tube. The array tube holder is then shifted to the other of the two positions to reverse the magnetic field. Alternatively, the magnetic field can be reversed by changing the position of the tubes, such as by rotating the tubes, preferably by rotating the tubes 180°. The magnetic field can also be reversed by moving the magnets, such as by shifting the magnets between the rows of wells or by changing the position of the magnets, preferably by flipping the magnets, more preferably by flipping the magnets 180°. The reversal of the magnetic field causes the magnetic particles to stream across the tube in the washing solution, preferably in a widest part of the tube, in response to the magnetic attraction of the magnet on the other side of the tube, thereby efficiently washing the magnetic beads in a short time, preferably about five seconds. The supernatant is removed and discarded and the process of reversing the magnetic field and washing the beads is preferably repeated, more preferably, the process is repeated about three times.

Further features and advantages of the invention, as well as the structure and operation of the invention, are described in detail below with reference to the accompanying drawings.

DETAILED DESCRIPTION OF THE PREFERRED EMBODIMENTS

The present invention is an apparatus for efficiently washing magnetic particles. One feature of a preferred embodiment is the provision of 108 wells. The 108 wells provide the ability to accommodate up to 108 tubes, preferably 0.2-ml tubes. The 108 wells also preferably permit an array of tubes, preferably an array of 96 tubes, to be moved between a first position and a second position. Another feature of this preferred embodiment is the asymmetrical location of five sets of 12 cylindrical rare-earth magnets. This design permits the rapid attraction of magnetic particles to the sides of the tubes such that a manual or robotic pipette tip can be inserted without disrupting the magnetic particle pellets. The geometry of the 108 wells and the asymmetrical location of the rare-earth magnets provide for the reversal of the magnetic field when moving the array of 96 tubes from the first position to the second position or vice versa. As will become apparent to one skilled in the art; the above features allow for the simultaneous washing of the magnetic particles in all 96 tubes of the array.

Alternatively, the magnetic field can be reversed by changing the position of the individual tubes, such as by rotating the tubes, preferably by rotating the tubes 180°. The magnetic field can also be reversed by moving the magnets, such as by shifting the magnets between the rows of wells or by changing the position of the magnets, preferably by flipping the magnets, more preferably by flipping the magnets 180°.

Although the present invention is described herein as being used to capture biotinylated cDNAs for cDNA molecule isolation, it will become apparent to one skilled in the art that the present invention can be used in any life sciences application, including molecular biology/immunology applications in which magnetic particles are used. Such applications include for example clinical diagnostic testing, i.e. with antibodies to sort cells, molecular biology, immunology and/or enzymology.

Figure 1:
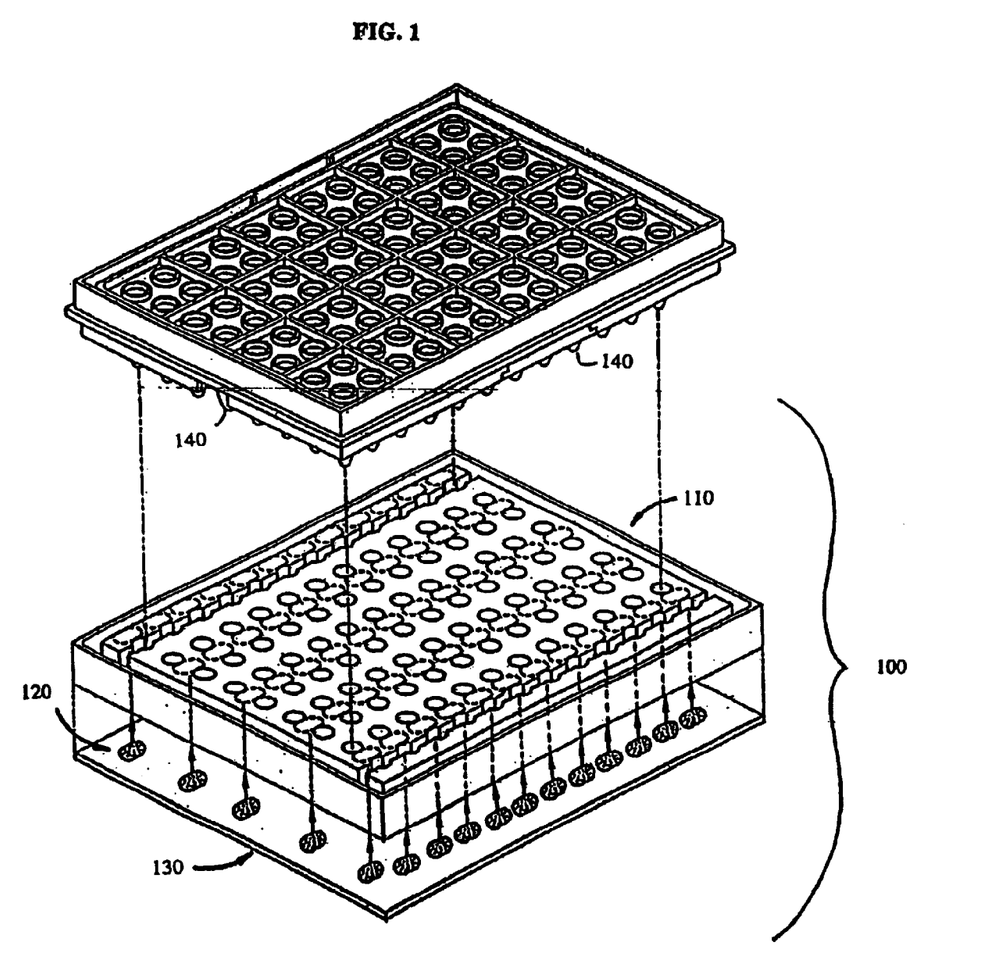
FIG. 1 is an exploded view of a preferred embodiment of the present invention, indicating the insertion of the magnets into the slots on the lower surface and the receipt of a 96 array tube holder with tubes onto the upper surface.

FIG. 1 is an exploded view of a preferred embodiment of the present invention. The apparatus 100 is preferably comprised of a well plate 110, a plurality of rare-earth magnets 120, and a base plate 130. The well plate 110 is provided to receive an array of 96 0.2-ml tubes 140 containing a solution of magnetic particles and to house the plurality of rare-earth magnets 120. Alternatively, the well plate 110 is equipped to receive anywhere from one to 108 0.2-ml tubes 140. The base plate 130 provides means for securing the plurality of rare-earth magnets 120 housed within the well plate 110. The base plate 130 is preferably an adhesive material, but can be any non-ferrous material that secures the rare-earth magnets 120 housed within the well plate 110.

Figure 2:
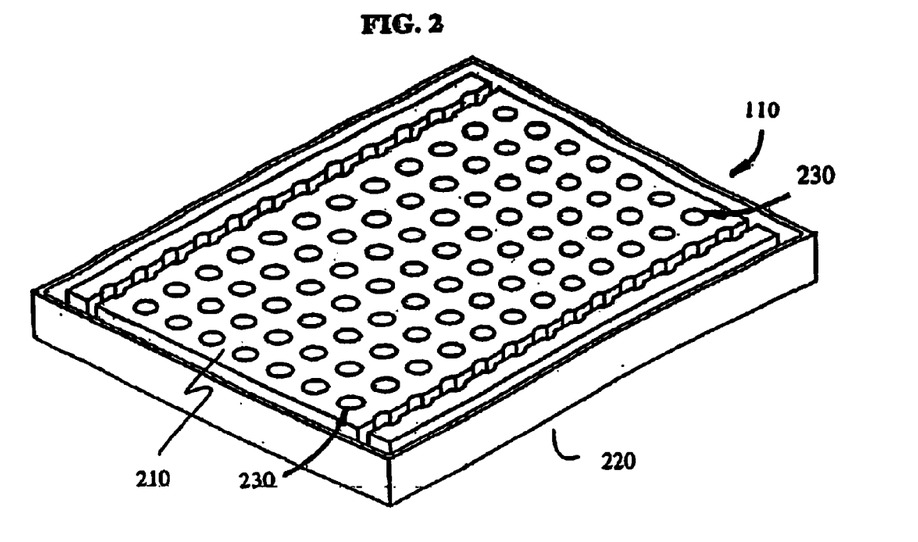
FIG. 2 is a perspective view of the preferred embodiment of the present invention.

FIG. 2 is a perspective view of well plate 110 according to a preferred embodiment. Well plate 110 is preferably comprised of a substantially flat upper surface 210, a substantially flat lower surface 220 (not directly shown from this view), and 108 wells 230 arranged in a 9×12 array. Five sets of 12 cylindrical rare-earth magnets 120 (not shown) are inserted within well plate 110. The well plate 110 is preferably composed of a white plastic material, such as acetal plastic. Alternatively, it would be apparent to those skilled in the art that other types of materials or plastic materials can be used for the well plate 110. Although any magnetic material can be used for the cylindrical rare-earth magnets 120, neodymium-iron-boron (Nd—Fe—B) is preferred.

In the preferred embodiment shown in FIG. 2, each of the 108 wells 230 has an opening in the upper surface 210 of the well plate that tapers conically toward a lower end to accommodate the array of 96 0.2-ml tubes 140 (not shown). Alternatively, well plate 110 could have wells of a variety of configurations depending on the type of test to be run in the apparatus 100. One skilled in the art will recognize that other well shapes capable of accommodating the array of 96 0.2-ml tubes 140, such as circular or rectangular wells, could also be used. The 108 wells 230 are preferably uniformly positioned in the upper surface 210.

Figure 3:
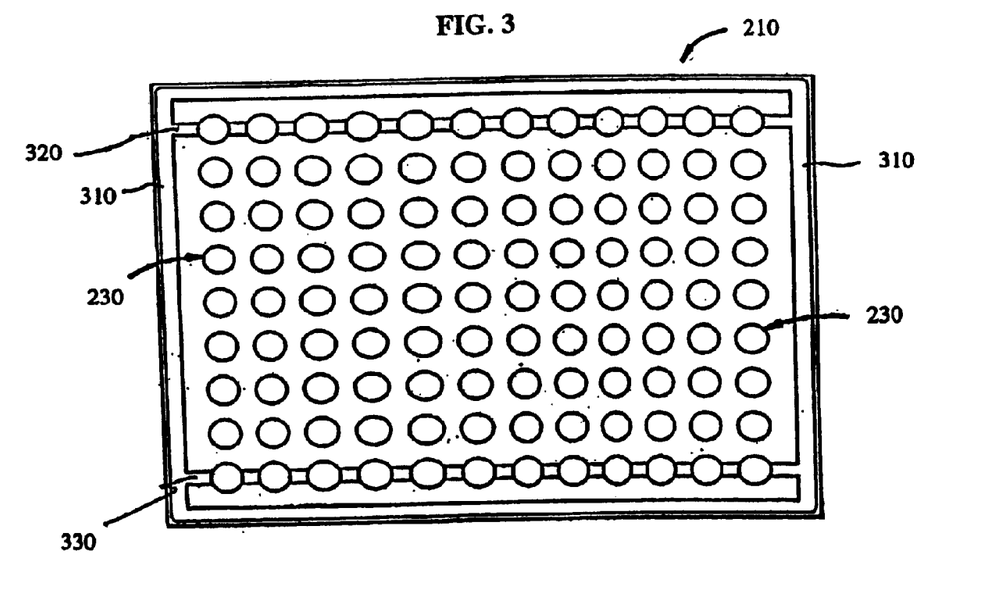
FIG. 3 is a top view of the upper surface of the preferred embodiment of the present invention.

The substantially flat upper surface 210 of the well plate 110 according to the preferred embodiment is shown in FIG. 3. The substantially flat upper surface 210 of the well plate 110 preferably uniformly positions the 108 wells 230 as an array of rows and columns (9 rows by 12 columns). The substantially flat upper surface 210 of the well plate 110 further comprises a recessed area 310 that extends around the perimeter of the well plate 110 and through the first row 320 and last row 330 of the 108 wells 230 for receipt of a 96 array tube holder (tray retainer set) manufactured by, for example, Perkin Elmer Corporation (Catalogue No.403081). Alternative embodiments may contain other forms of recessed areas for accommodating other models of array tube holders or no recessed area at all.

Figure 4:
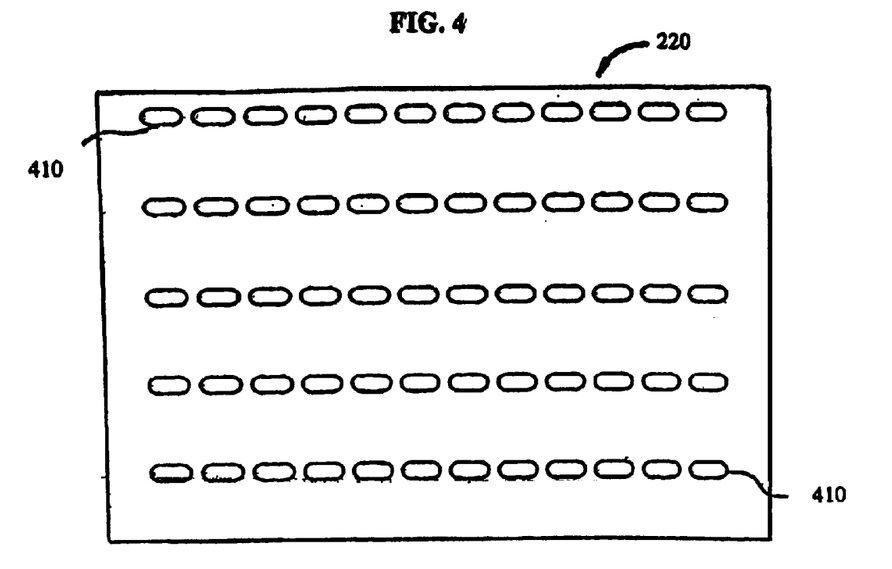
FIG. 4 is a bottom view of the lower surface of the preferred embodiment of the present invention illustrating magnet slots 410.

The substantially flat lower surface 220 of well plate 110 according to the preferred embodiment is shown in FIG. 4. The substantially flat lower surface 220 is comprised of a plurality of cylindrical slots 410. The plurality of cylindrical slots 410 are preferably positioned asymmetrically in an array format of rows and columns. Each of the cylindrical slots 410 is used to house one of the rare earth magnets 120 (not shown).

In an alternative embodiment (not shown), the substantially flat lower surface 220 of the well plate 110 is comprised of elongated slots, preferably five elongated slots, each row having one slot. The elongated slots are positioned asymmetrically in an array format of rows, preferably five rows, and one column. Each of the elongated slots is used to house one bar magnet. Each elongated slot and bar magnet extends the approximate length of the well plate 110.

Figure 5:
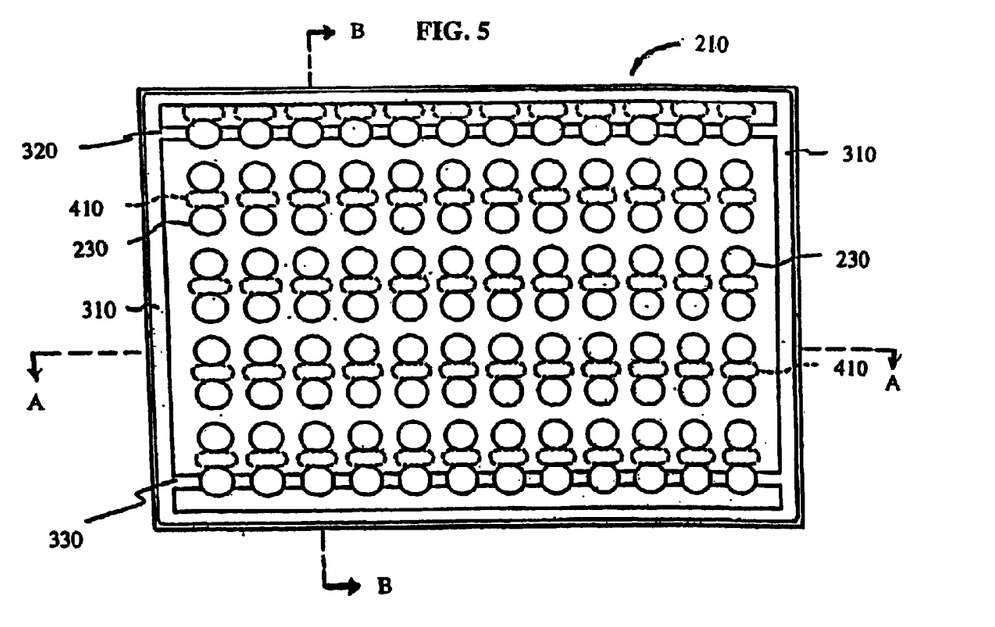
FIG. 5 is a top view of the upper surface including a projected-view of magnet slots 410 from the lower surface of the preferred embodiment of the present invention.

The relative positioning of the plurality of cylindrical slots 410 with respect to each of the 108 wells 230 according to a preferred embodiment will now be described with reference to FIG. 5. FIG. 5 is a top view of the substantially flat upper surface 210 of well plate 110 with the positions of the plurality of slots 410 from the substantially flat lower surface 220 shown in dotted lines on the upper surface 210. The first row of twelve (12) cylindrical slots 410 is positioned between the upper edge of the long axis of the well plate 110 and the first row 320 of wells 230. The remaining four (4) rows of twelve (12) cylindrical slots 410 are positioned along the long axis of the well plate 110 between the remaining 8 rows of wells 230. Thus, each well 230 is adjacent to one side of cylindrical slot 410.

Figure 6:
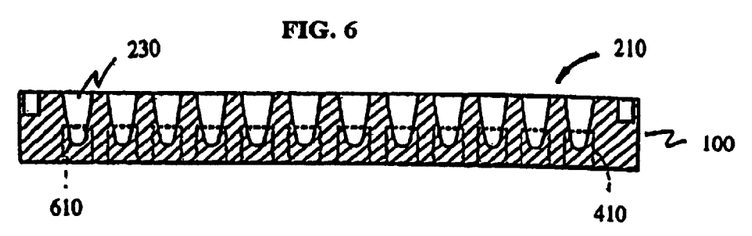
FIG. 6 is a cross-sectional view of the preferred embodiment of the present invention taken across line A—A of FIG. 5.

The five sets of cylindrical rare-earth magnets 120 are inserted in the plurality of cylindrical slots 410. FIG. 6 represents a cross-sectional view of the well plate 110 taken across line A—A of FIG. 5. The projection of the plurality of cylindrical slots 410 are indicated by the dotted lines. FIG. 6 also indicates in dotted lines the placement 610 of each cylindrical rare-earth magnet 120 inside each slot 410. Each cylindrical rare-earth magnet 120 is placed adjacent to a well 230 in order to attract the magnetic particles contained in a tube 140 (not shown) inserted in the well 230 to one side of the wall of the tube 140.

Figure 7:
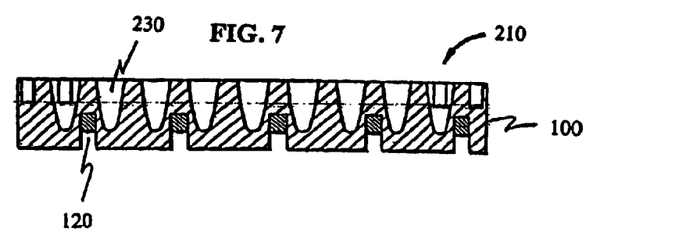
FIG. 7 is a cross-sectional view of the preferred embodiment of the present invention taken across line B—B of FIG. 5.
Figure 10A:
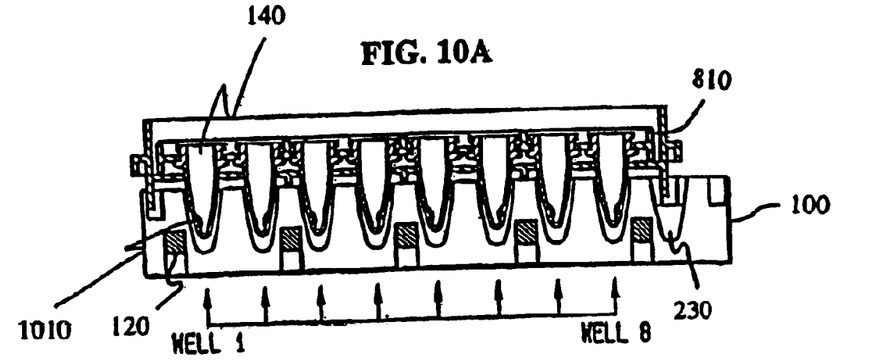
FIG. 10A is a cross-sectional view of the preferred embodiment of the present invention taken across line B—B of FIG. 5 with the insertion of a 96 array tube holder with tubes in a first position for washing the magnetic particles.
Figure 10B:
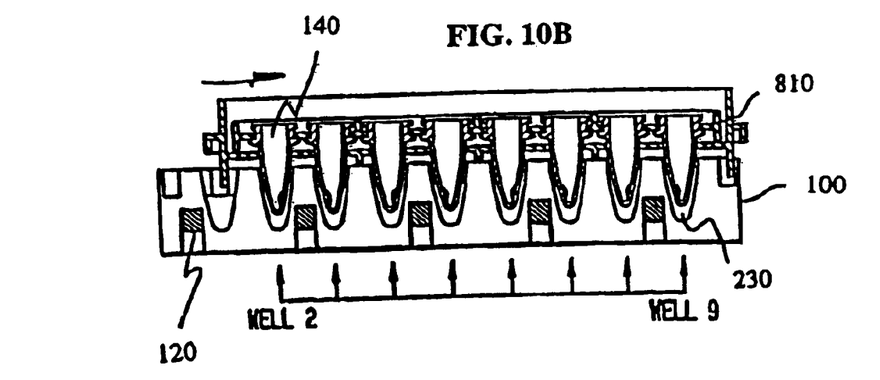
FIG. 10B is a cross-sectional view of the preferred embodiment of the present invention taken across line B—B of FIG. 5 with the insertion of a 96 array tube holder with tubes in a second position for washing the magnetic particles.

FIG. 7 illustrates a cross-sectional view of the well plate 110 taken across line BB of FIG. 5. The asymmetrical placement of the cylindrical rare-earth magnets 120 are shown in relation to each well 230. As shown in FIGS. 10A and 10B, the placement of the cylindrical rare-earth magnets 120 causes the magnetic particles inside of a tube 140 to be attracted to opposite sides of the tube 140 for adjacent rows.

Figure 8:
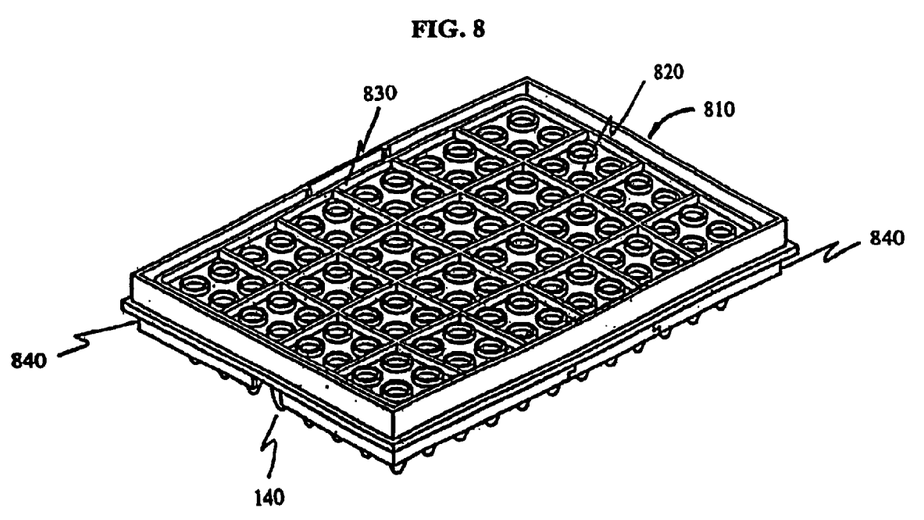
FIG. 8 is a perspective view of a 96 array tube holder holding tubes.

FIG. 8 represents a 96 array tube holder 810 with tubes 140 according to a preferred embodiment, such as the 96 tube tray retainer set manufactured by Perkin Elmer Corporation. The 96 array tube holder 810 is a two-piece plastic tube holder. The bottom piece 820 of holder 810 allows for 1 to 96 tubes 140 or up to an 8 by 12 array of tubes 140 to be inserted into holder 810. The top piece 830 of holder 810 secures tubes 140 by clamping tubes 140 within holder 810. Holder 810 further comprises brackets 840 surrounding bottom piece 820. The recessed area 310 of the well plate 110 is designed to accept brackets 840 surrounding bottom piece 820 in either of two positions (described further herein).

Figure 9A:
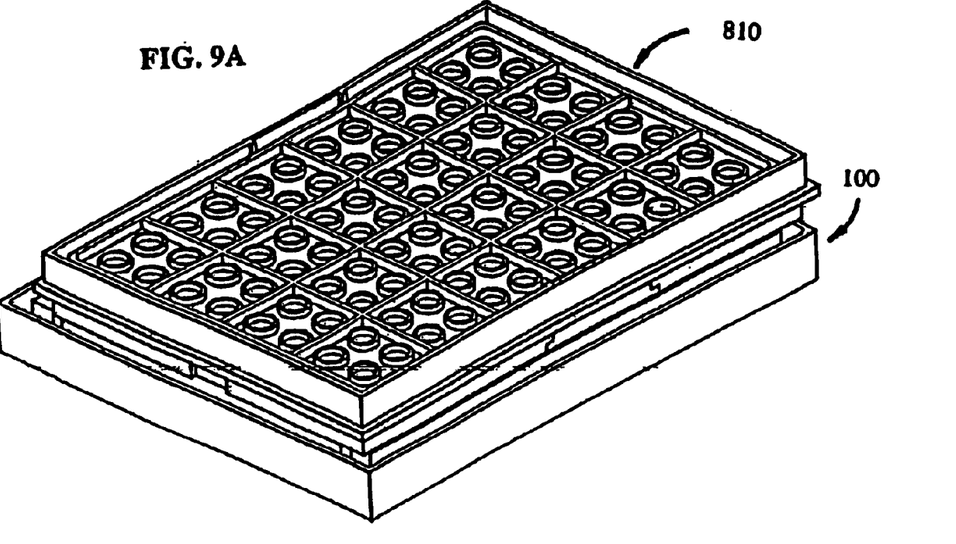
FIG. 9A is a perspective view of the preferred embodiment of the present invention receiving a 96 array tube holder with tubes in a first position for washing the magnetic particles.
Figure 9B:
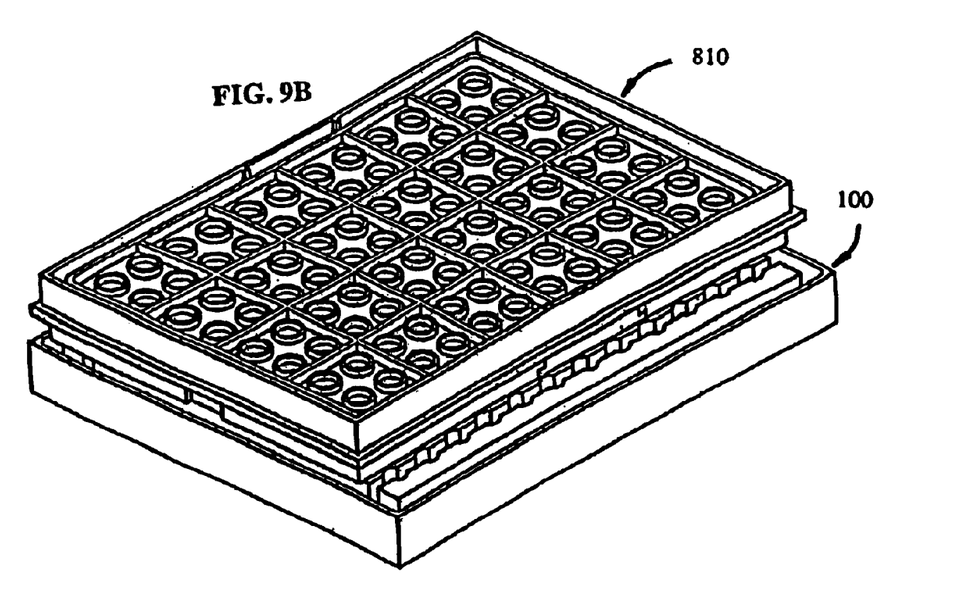
FIG. 9B is a perspective view of the preferred embodiment of the present invention receiving a 96 array tube holder with tubes in a second position for washing the magnetic particles.

The well plate 110 9×12 array of wells 230 allows the 8×12 tube holder 810 to be placed in one of two positions. FIGS. 9A and 9B illustrate the insertion of tube holder 810 into apparatus 100 in first and second positions, respectively. In FIG. 9A, holder 810 with tubes 140 is positioned in the first position. In FIG. 9B, holder 810 with tubes 140 is positioned in the second position. Note that the first position and the second position are interchangeable such that FIG. 9B could represent holder 810-with-tubes 140 positioned in the first position and FIG. 9A could represent holder 810 with tubes 140 positioned in the second position.

The ability of the present invention to simultaneously wash the magnetic beads in all of the 96 tubes 140 according to the preferred embodiment is directly correlated to the additional row of wells 230 (i.e., 9 rows in well plate 110, as compared to 8 rows in array tube holder 810), the asymmetrical positioning of slots 420 in which rare-earth magnets 120 are inserted, and the ability to reverse the magnetic field by shifting the 96 tube array tube holder 810 with tubes 140 from the first position to the second position (and vice versa). The operation of the present invention will now be described with reference to FIGS. 10A and 10B.

FIG. 10A represents a cross-sectional view of apparatus 100 taken across line B—B of FIG. 5 with tube holder 810 inserted in apparatus 100 in a first position. As shown, apparatus 100 contains an additional row of wells 230 as compared to tube holder 810. The magnetic particles in solution in each tube 140 are shown as magnetic beads 1010 attracted to the walls of tubes 140. The magnetic beads 1010 are attracted to the tube walls adjacent to the rare-earth magnets 120 and are held onto the tube 140 walls by the magnetic field. Thus, each adjacent tube 140 has magnetic beads 1010 attracted to opposite sides of the walls of tubes 140. The attachment of the magnetic beads 1010 onto the sides of the tube 140 walls allows for the insertion of a manual or robotic pipette tip into each tube 140 without disrupting the magnetic beads 1010. Therefore, supernatant material can be removed and solutions can be added without disturbing the magnetic beads 1010.

After the removal of the supernatant from each of the tubes 140, a washing solution is added to each of the tubes 140. The 96 tube array tube holder 810 with tubes 140 is then shifted to a second position. FIG. 10B represents a cross-sectional view of apparatus 100 taken across line B—B of FIG. 5 with tube holder 810 inserted in apparatus 100 in the second position. The rare-earth magnets 120 are now located on the opposite side of each tube 140. The magnetic field is therefore reversed, and because of the position of the magnets 120 relative to the tubes 140, the magnetic particles stream across the widest diameter of the washing solution because of the attraction of the magnetic field. The supernatant is removed and more washing solution is added. The process is preferably repeated a plurality of times. For example, the process may be repeated as many times as is necessary to achieve the required amount of washing.

With regards to the approach for cDNA molecule isolation, the use of the present invention reduces the washing process from approximately 45 minutes for six 1.7 ml tubes to approximately 5 minutes for 96 0.2 ml tubes. The need for individual finger tapping or vortexing of the tubes containing the paramagnetic beads is eliminated. During the extensive washing process of the cDNA Capture procedure, the time in which the tubes are placed in apparatus 100 is reduced from 2 minutes to 5 seconds. According to a preferred embodiment, the extensive washing process is repeated for a total of three (3) times. Where the cDNA Capture procedure requires 5 minute stays in the magnet, the present invention reduces the length of time in apparatus 100 to about one (1) minute. The amount of washing solution needed to wash the magnetic particles is also reduced with apparatus 100.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. An apparatus for washing or manipulating magnetic particles said apparatus comprising:
    a) a well plate for receiving an array tube holder having x rows of tubes, each tube containing magnetic particles, said well plate having an upper surface, a lower surface, and (x+1) rows of wells for shifting said array tube holder from a first position to a second position in said well plate;
    b) ((x/2)+1) rows of magnets asymmetrically positioned within said well plate, wherein a first row of magnets is adjacent to tubes in a first row of wells and (x/2) rows of magnets are positioned between x remaining rows of wells; and
    c) base plate attached to said lower surface of said well plate for securing said magnets to said well plate;
    whereby placing said array tube holder in said first position causes magnetic fields produced by said magnets to attract the magnetic particles in adjacent rows of tubes to one side of said tubes, and shifting said array tube holder to said second position reverses said magnetic fields causing said magnetic particles to move across to the other side of said tubes.

2. The apparatus of claim 1, wherein said base plate is adhesively attached to said lower surface.

3. The apparatus of claim 1, wherein each of said wells in said well plate has an opening in said upper surface that tapers conically toward a lower end.

4. The apparatus of claim 1, wherein said upper surface has a recessed area around the perimeter and through said first row and a last row of wells for receiving said array tube holder in one of said first and said second positions.

5. The apparatus of claim 1, wherein said array tube holder is a 96 tube array tube holder having 8 rows and 12 columns.

6. The apparatus of claim 5, wherein said well plate comprises 108 wells having 9 rows and 12 columns.

7. The apparatus of claim 1, wherein said tubes are 0.2-ml tubes.

8. The apparatus of claim 1, wherein said well plate is comprised of acetyl plastic.

9. The apparatus of claim 1, wherein said magnets are comprised of neodymium-iron-boron.

10. An apparatus for washing magnetic particles, said apparatus comprising:
    a) a well plate having an upper surface, a lower surface, and a plurality of wells uniformly positioned in (x+1) rows by y columns, each of said wells having an opening in said upper surface that tapers conically toward a lower end, said lower surface having a plurality of slots asymmetrically positioned in ((x/2)+1) rows by y columns, wherein a first row of said slots is positioned adjacent to a first row of wells and subsequent rows of said slots are positioned between remaining rows of wells, said well plate receiving an x by y array tube holder with tubes containing magnetic particles;
    b) a plurality of magnets, each of said magnets being inserted into each of said slots in said lower surface of said well plate and positioned adjacent to said lower end of each of said wells for attracting said magnetic particles in said tubes toward one side of each tube; and
    c) a base plate attached to said lower surface of said well plate for securing said magnets,
    wherein said magnetic particles attracted to one side of said tubes are washed by shifting said array tube holder from a first position to a second position to reverse the magnetic field, causing the magnetic particles to move across to the other side of the tube.

* * * * *